United States Patent [19]

Ching et al.

[11] Patent Number: 5,770,389
[45] Date of Patent: *Jun. 23, 1998

[54] APPARATUS AND METHOD FOR DETERMINING THE QUANITY OF AN ANALYTE IN A BIOLOGICAL SAMPLE BY MEANS OF TRANSMISSION PHOTOMETRY

[75] Inventors: Shan-Fun Ching, Libertyville; Joanell Veronica Hoijer, Arlington Heights; Donald Irvine Stimpson, Gurnee; Julian Gordon, Lake Bluff, all of Ill.

[73] Assignee: Abbott Laboratories, Abbott Park, Ill.

[ * ] Notice: The term of this patent shall not extend beyond the expiration date of Pat. No. 5,387,790.

[21] Appl. No.: 601,514

[22] Filed: Feb. 14, 1996

Related U.S. Application Data

[63] Continuation of Ser. No. 127,387, Sep. 27, 1993, abandoned.
[51] Int. Cl.$^6$ ...................... G01N 33/543; G01N 33/558
[52] U.S. Cl. .......................... 435/7.92; 307/311; 377/12; 377/20; 377/53; 377/58; 356/432; 356/433; 356/434; 250/214 RC; 250/214 LS; 250/214 SW; 250/214 A; 422/56; 422/57; 422/82.05; 422/80.08; 435/287.1; 435/287.2; 435/287.7; 435/810; 436/514; 436/518; 436/805; 436/810
[58] Field of Search ............................. 307/311; 377/12, 377/20, 53, 58, 95; 356/432–434; 250/214 RC, 214 LS, 214 SW, 214 A, 214 PR, 214.1; 422/56, 57, 82.05, 82.08, 82.09, 82.01, 82.02; 435/7.9, 7.92, 7.93, 7.94, 11, 14, 287.1, 287.2, 287.7, 287.9, 805, 808, 810, 970; 436/46, 50, 66, 164, 169, 172, 514, 518–520, 524, 525, 527, 528, 531, 533, 534, 805, 807, 808, 810

[56] References Cited

U.S. PATENT DOCUMENTS

| 4,097,732 | 6/1978 | Krause et al. ........................ 250/205 |
|---|---|---|
| 4,275,149 | 6/1981 | Litman et al. .............................. 435/7 |
| 4,366,241 | 12/1982 | Tom et al. .................................. 435/7 |
| 4,487,839 | 12/1984 | Kamentsky ............................. 436/518 |
| 4,637,978 | 1/1987 | Dappen ..................................... 436/11 |
| 4,750,838 | 6/1988 | De Wolf et al. ........................ 356/445 |
| 4,756,828 | 7/1988 | Litman et al. .............................. 435/7 |
| 4,757,004 | 7/1988 | Houts et al. ................................ 435/7 |
| 4,786,797 | 11/1988 | Ely ......................................... 307/311 |
| 4,954,452 | 9/1990 | Yost et al. ............................... 435/524 |
| 5,120,643 | 6/1992 | Ching et al. ........................... 435/7.92 |
| 5,229,073 | 7/1993 | Luo et al. ................................. 422/56 |
| 5,252,459 | 10/1993 | Tarcha et al. .............................. 435/6 |
| 5,304,468 | 4/1994 | Phillips et al. ........................... 435/14 |
| 5,387,790 | 2/1995 | Stimpson ................................. 250/214 |

FOREIGN PATENT DOCUMENTS 0063810   11/1982   European Pat. Off. .

OTHER PUBLICATIONS

Towbin, H. and Gordon, J. "Immunoblotting and Dot Immunobinding—Curent Status and Outlook." *Journal of Immunological Methods* vol. 72 (1984) pp. 313–340.

*Primary Examiner*—Christopher L. Chin
*Attorney, Agent, or Firm*—David L. Weinstein

[57] ABSTRACT

A device and method for quantitative determination of an analyte in a biological sample utilizes a non-transparent support medium for retaining a chromatogenic reaction product with the medium being exposed to a source of light for transmitting therethrough a scattered, uniform response light signal which is collected at a photosensitive device whereby the amount of the analyte is correlated to the intensity of the response light signal. The response light signal may be converted to a time-duration signal proportional to light intensity to facilitate the quantitative determination.

38 Claims, 3 Drawing Sheets

APPARATUS AND METHOD FOR DETERMINING THE QUANITY OF AN ANALYTE IN A BIOLOGICAL SAMPLE BY MEANS OF TRANSMISSION PHOTOMETRY

This application is a continuation of application Ser. No. 08/127,387, filed Sep. 27, 1993, now abandoned.

FIELD OF INVENTION

The invention is generally related to an apparatus and a method for the quantitative determination of clinically relevant analytes useful in the diagnosis of disease or wellness, by means of photometry using non-transparent membranes.

DESCRIPTION OF THE PRIOR ART

Traditionally clinical chemistry measurements have been made by spectrophotometry of solution phase reaction products In fact, classical clinical chemistry is largely based on the development of spectrophotometer apparatus and techniques.

Immunoassays using enzyme-based signal amplification have been adapted to spectrophotometry with color generating reactions such as those of alkaline phosphatase and horse radish peroxidase with appropriate chromogenic substrates. Photometry is done by transmission through transparent solutions in cuvette-based photometers (e.g., Abbott Quantum), or using transmission reads with multiwell detection on microtiter plates (e.g., Dynatec Titerteck, Molecular Biosystems).

All of these involve simple multi-step additions and reactions resulting in a well-defined colored product in solution, depending on the amount of the analyte. Clinical chemistry assays have also been adapted to dipstick or strip type detection with reactants dried into the strips, and products of these can be read on commercially available systems, such as the Ames Chemstix or the Boeringer/Mannheim Reflotron, the latter dependent upon the reflectance measurements on a solid phase of filter paper or membrane. Immunoassays can also be done in simplified formats by generating a colored or chromogenic reaction product on solid phase membranes, the earliest of which is the Dot Immunobinding assay of Gordon et al (European Patent Application 0 063 810). Reflectance measurements was the preferred mode, and is described in detail therein, as well as a computer program adapting the use of a commercial thin-layer chromatogram scanner for reading such dot immunoassays [H.Towbin & J.Gordon: Immunoblotting and Dot Immunobinding-Current Status and Outlook, Journal of Immunological Methods,72(1984) 313–340]. More advanced immunoassays based on rapid development of color on the surface of a flow-through filtration device (e.g., Hybritech Icon) are also quantitated by means of simple reflectance measurements.

Thus, there are two widely used kinds of photometric measurement techniques in diagnostic testing: (1) solution phase (where the solution must be clear for accurate determinations and minimum interference from light scattering); or (2) reflectance from non-transparent porous solid phases, in dipstick or self-performing assays where a chromatographic or filtration medium is used as a support for onboard reagents, as well as a support for the development of color. The latter have been used only with reflectance determination because of the widely perceived inability to make photometric determinations through a membrane or filter, which, even if not opaque, are highly light-scattering media and so do not lend themselves to well controlled classical optical designs using lenses and collimation.

One attempt made to control for light scattering in liquids is the HemoCue (Hemocue AB, Heisingborg, Sweden) hemoglobin reader. This device uses dual wavelength determination on and adjacent to the hemoglobin peak, to provide a correction factor for light scattering from lipemic samples. None of the above suggests any need or advantage in measuring transmission on membrane or filter material used as solid phases in assays.

Self-performing immunoassays have come to the forefront with the advent of immunochromatographic strip formats and directly visualizable color readout, as the Abbott Test Pack Plus device (Abbott Laboratories, Abbott Park, Ill.). However, commercial applications have been limited to qualitative visual readout, partly due to the difficulty of obtaining precise numeric results from color deposited on a solid phase. One solution has been to perform semiquantitative determinations with successive bands on an immunochromatographic strip acting as titration for varying levels of analyte. Thus, a thermometer-type readout can be used for an approximate visual quantitation. See, for example U.S. Pat. No. 4,756,828; 4,757,004; "One-Step Competitive Immunochromatographic Assay for Semiquantitative Determination of Lipoprotein(a) in Plasma", Clinical Chemistry, 39, 619–624(1993), S. C. Luo et. al.; U.S. Pat. No. 5,229,073; and U.S. Pat. No. 5,073,484.

SUMMARY OF THE INVENTION

The subject invention is based on the discovery that a small light source may be placed in close proximity on one side of support medium carrying a chromogenic reaction product, with a detector placed in close proximity on the other side to make reliable photometric determinations. Because of the highly light-scattering nature of the medium, the light, exiting from the opposite side of the support medium, defines a uniform light signal.

Suprisingly, the uniformity eliminates the necessity for any focussing or lensing devices, and the proximity permits the efficient utilization of the light from a relatively low power source. The invention can be applied equally well to clinical chemistry liquid phase color development, where the support medium simply acts as a cuvette (albeit highly scattering) for metering and optical path-length determination. Further aspects of the present invention are the use of automatic light intensity adjustment in a low signal part of the support medium to establish a baseline, and automatic voltage adjustments of intensity to maintain the signal within the linear range of the light-source-detector combination.

A further aspect of the present invention is a simplified analogue to digital conversion achieved by measurement of resistivity of the photodetector element by the direct measurement of the time constant of a capacitator-resistance circuit and conversion of a signal into digitized time units. Additional features of the invention are use of an internal control assay on the same strip, and using a ratio determination between the signal from the analyte capture zone and the internal control capture zone to provide experimental values corrected for various forms of variation. Another feature of the invention lies in the ability to perform quantitation determinations on freshly run assay strips (wet mode) or on dried assay strips at any time after completion of the assay (dry mode).

The automatic light intensity variation feature will automatically correct for the difference in the background scattering between the wet and the dry medium. A further feature of the invention is the elimination or reduction of the effect of spurious reflections from optical interfaces or plastic housings, when transmission mode is used.

It is, therefore, an object and feature of the invention to provide an apparatus and a method for making a quantitative determination of an analyte in a biological sample by correlating the color development by a chromogenic reaction product in a highly light-scattering support medium.

It is another object and feature of the invention to provide a support medium for receiving and retaining an analyte from a biological sample, the medium is adapted for receiving a source light signal and transmitting therethrough a response light signal altered from the source light signal by the presence of a chromogenic reaction product derived from, and representative of the amount of, the analyte in the sample.

It is a further object and feature of the invention to provide an apparatus and a method for making a quantitative determination of the amount of an analyte, in a biological sample, by measuring the time duration of the discharge cycle of a capacitor network in response to the intensity of a response light signal, wherein the light intensity of the response light signal is related to the amount of the analyte by means of the production, or presence, of a chromogenic reaction product.

Other objects and features of the invention will be readily apparent from the accompanying drawings and detailed description of the preferred embodiment.

DETAILED DESCRIPTION OF THE PREFERRED EMBODIMENT

There are numerous light intensity detection circuits typically using a photosensitive element which is capable of generating a varying voltage signal which is then amplified and converted to a digital signal to be processed to make a quantitative determination based on light intensity. This is then compared with a reference to evaluate the results. While the subject invention has been found to be particularly well suited for use in a light intensity detection system which relies on a time duration signal generated by measuring the variable resistance of a photosensitive element in response to intensity of the received light signal, it will be readily understood by those skilled in the art that other known circuits could be substituted without departing from the quantitative determination aspects of the invention.

Figure 1:
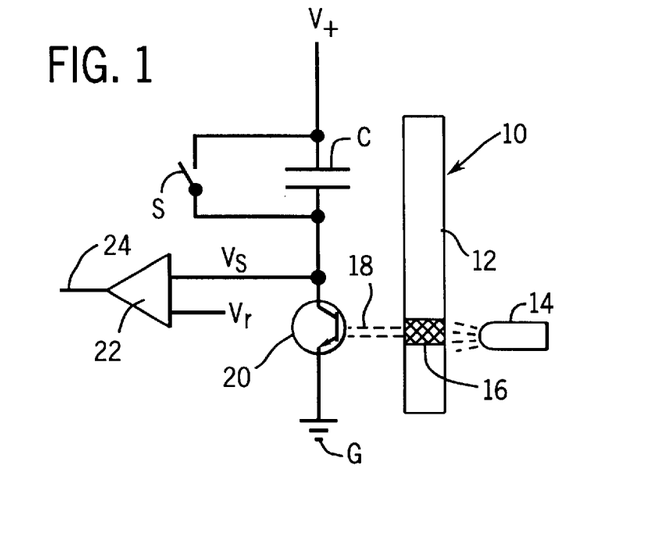
FIG. 1 diagramatically illustrates a basic system incorporating the teachings of the invention, including the photometric determination circuit and the support medium.

With specific reference to the drawings, a diagramtic illustration of a time-duration light detection circuit used in conjunction with the subject invention is shown in FIG. 1. This circuit is more completely described in the co-pending application entitled: "LIGHT INTENSITY DETECTION AND MEASURING CIRCUIT", (U.S. Pat. No. 5,387,790), filed on even date herewith and assigned to the assignee hereof, and incorporated by herein reference.

As shown in FIG. 1, a typical analyte or sample to be analyzed utilizing light intensity is designated by the reference numeral 10 and includes a support medium 12, at least a portion of which is adapted for transmitting light from a referenced source such as the LED 14. The sample analyte 16 is positioned to receive the light emitted from the source 14. The presence of a chromogenic reaction product impacts the intensity of the light passing therethrough, and the transmitted light, as indicated at 18 is uniformly scattered and is received by a collector or control element such as the photosensitive device or phototransistor 20. In typical manner, the phototransistor 20 develops a variable resistance dependent upon the intensity of the light of the scattered beam 18. Typically, as the scattered beam 18 increases in intensity, the resistance of the phototransistor 20 decreases.

The phototransistor 20 is part of an electrical circuit having a source voltage as indicated by the voltage source V+. In typical operation, the voltage source is a low voltage (5 vdc) power supply. A capacitor C is positioned in series in the network comprising the voltage source, the capacitor, and the phototransistor. In the preferred embodiment, a switching network S is coupled in parallel across the capacitor and can be used to bypass the capacitor.

In operation, the capacitor C is initially charged. The scattered light beam 18 is then collected on the phototransistor 20, to control the resistance therethrough. The switch S is then opened, allowing the capacitor to discharge through the phototransistor. The capacitor will discharge over a time cycled duration, in accordance with the inverse product of the capacitance and the resistance generated by the phototransistor, or 1/RC in the well known manner.

In the preferred embodiment, the voltage signal present during the charge up cycle is measured and picked off of the circuit as indicated by Vs. This is introduced into an operational amplifier 22 along with a reference signal Vr. The combined signal is introduced to a microprocessor or other computer driven system, as indicated at 24.

The time-to-charge (TTC) the capacitor C is equal to the inverse of the product of the resistance R and the capacitance C multiplied by the natural log of the signal Vr over the source voltage V+, or:

$$TTC = \frac{1}{RC} \ln \frac{Vr}{Vt}$$

Figure 2:
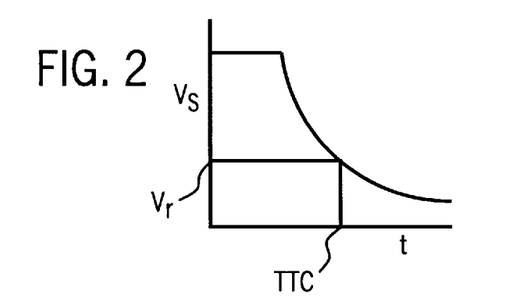
FIG. 2 is a graph showing the correlation of the charge network and time duration signal to the intensity of the collected light signal.

By monitoring the time-to-charge (TTC), the intensity of the light can be determined. A graph illustrating this is shown in FIG. 2. As there shown, the time duration signal Vs is measured along the vertical axis and the time-to-charge (TTC) is measured along the horizontal axis, where:

$$Vs = V + (e^{-RCt}).$$

Figure 3:
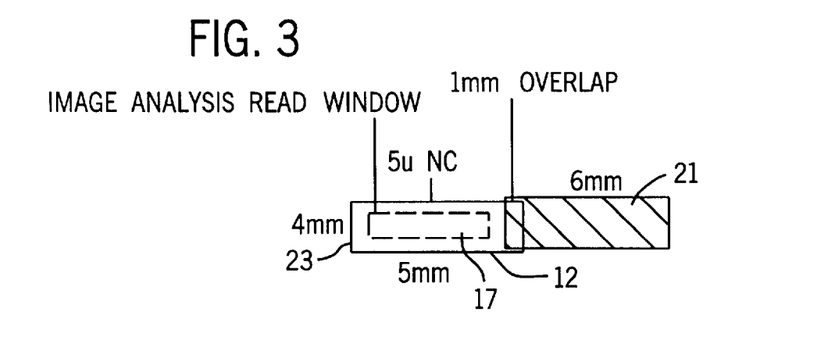
FIG. 3 illustrates a reagent pad as incorporated in a support medium for exposing an analyte to transmission photometry in accordance with the present invention.

A support medium 10 for supporting the analyte 16 in accordance with the teachings of the present invention is shown in detail in FIG. 3. The support medium 10 can be a chromatographic material comprising any suitably absorbent, porous or capillary possessing material through which a solution containing analyte can be transported by wicking action. The support medium need not be of the chromatographic type. The support medium must be able to highly scatter light and to retain the analye or the chromogenic reaction product in a localized area for detection.

Natural, synthetic, or naturally occurring materials that are synthetically modified, can be used as the chromatographic material including, but not limited to: cellulose materials such as paper, cellulose, and cellulose derivatives such as cellulose acetate and nitrocellulose; fiberglass; cloth, both naturally occurring (e.g., cotton) and synthetic (e.g., nylon); porous gels such as silica gel, agarose, dextran, and gelatin; porous fibrous matrixes; starch based materials, such as Sephadex® brand cross-linked dextran chains; ceramic materials; films of polyvinyl chloride and combinations of polyvinyl chloridesilica; and the like. The chromatographic materials should not interfere with the production of a detectable signal. The chromatographic material should have a reasonable inherent strength, or strength can be provided by means of a supplemental support, provided, that it does not adversely affect the light transmission properties of the medium.

A preferred chromatographic material is nitrocellulose. When nitrocellulose is used, however, the material of the application pad should be chosen for its ability to premix the liquid, biological test (analyte containing) sample with the at least one assay reagent contained therein, i.e., fluid-flow through a nitrocellulose membrane is laminar and does not provide, within the chromatographic material, the more turbulent flow characteristics which are necessary for the initial mixing of test sample and application pad reagent(s). If nitrocellulose is used as the support medium, Porex® hydrophilic polyethylene frit or glass fiber filter paper are appropriate materials for the application pad 21 because they enable the mixing and reaction of the test sample and application pad reagents within the application pad before transfer to the chromatographic material occurs. Especially preferred for use as the support medium are nitrocellulose laminated strips and glass fiber filter paper.

The particular dimensions of the support medium will be a matter of convenience, depending upon the size of the test sample involved, the assay protocol, the means for detecting and measuring the signal, and the like. For example, the dimensions may be chosen to regulate the rate of fluid migration as well as the amount of test sample to be imbibed by the chromatographic materials.

A "specific binding member", as used herein, is a member of a specific binding pair, i.e., two different molecules wherein one of the molecules through chemical or physical means specifically binds to the second molecule. In addition to antigen and antibody specific binding pairs, other specific binding pairs include, as examples without limitation, biotin and avidin, carbohydrates and lectins, complementary nucleotide sequences such as the probe and capture nucleic acids used in hybridization reactions with a target nucleic acid sequence as the analyte, complementary peptide sequences, effector and receptor molecules, enzyme cofactors and enzymes, enzyme inhibitors and enzymes, a peptide sequence and an antibody specific for the sequence or the entire protein, and the like. Furthermore, specific binding pairs can include members that are analogs of the original specific binding member, for example an analyte-analog. If the specific binding member is an immunoreactant it can be, for example, an antibody, antigen, hapten, or complex thereof, and if an antibody is used, it can be a monoclonal or polyclonal antibody, a recombinant protein or antibody, a mixture(s) or fragment(s) thereof, as well as a mixture of an antibody and other specific binding members. The details of the preparation of such antibodies and their suitability for use as specific binding members are well known to those skilled in the art.

An "analyte", as used herein, is the compound or composition to be detected or measured in the test sample. In a binding assay, the analyte will have at least one epitope or binding site for which there exists a naturally occurring, complementary specific binding member or for which a specific binding member can be prepared. "Analyte" also includes any antigenic substances, haptens, antibodies, and combinations thereof. The analyte of interest in an assay can be, for example, a protein, a peptide, an amino acid, a nucleic acid, a hormone, a steroid, a vitamin, a pathogenic microorganism for which polyclonal and/or monoclonal antibodies can be produced, a natural or synthetic chemical substance, a contaminant, a drug including those administered for therapeutic purposes as well as those administered for illicit purposes, and metabolites of or antibodies to any of the above substances.

Illustrative of the so-called "drugs of abuse" which are suitable as analytes for this invention are the following: codeine, morphine, heroin, cocaine (and its metabolite benzoylecgonine), inethamphetamine, phencyclidine, phenothiazines, tetrahydrocannabinol and the like. Illustrative of the therapeutic and/or prophylactic pharmaceutical agents, which are suitable for detection or measurement by the present invention, are theophylline, digoxin, digitoxin, gentamicin, tobramycin, amikacin, kanamycin, netilmicin, streptomycin, phenobarbital, dilantin, procainamide, N-acetylprocainamide, lidocaine, quinidine, propranolol, ethosuximide, acetaminophen, acetylsalicylic acid, carbamazepine-primidone, valproic acid, methotrexate, dibekacin-chloramphenicol, vancomycin, disopyramide, amitriptyline, desipramine, imipramine, nortriptyline and the like.

Examples of the hormones which are suitable as analytes for this invention are the following: thyroid stimulating hormone (TSH), human chorionic gonadotropin (hCG), luteinizing hormone (LH). and follicle stimulating hormone (FSH). An especially preferred hormone analyte in pregnancy testing is hCG.

Pathogenic microorganisms suitable for analysis by the present invention include those microorganisms disclosed in U.S. Pat. No. 4,366,241, which is herein incorporated by reference. Illustrative of some of these microorganisms are those associated with urinary tract infections, such as *Streptococcus pyogenes, Streptococcus salivarus, Escherichia coli, Staphylococcus aureus, Klebsiella pneumonia, Proteus mirabilis* and the like. The microorganisms, when assayed by the present invention, may be intact, lysed, ground or otherwise fragmented and the resulting composition or portion thereof assayed. Preferably, the microorganisms are assayed intact.

The term "analyte-analog", as used herein, refers to a substance which cross-reacts with an analyte-specific binding member, although it may do so to a greater or a lesser extent than does the analyte itself. The analyte-analog can include a modified analyte as well as a fragmented or synthetic portion of the analyte molecule so long as the analyte-analog has at least one epitopic site in common with the analyte of interest.

"Chromogenic reaction product", as used herein, is a substance or assay reaction product formed as a result of a chemical or immunological reaction between the analyte or analyte-analog and the various reagent used in the assay. The chromogenic reaction product, a chromophore, is able to produce a colored detectable signal.

"Fluorogenic reaction product", as used herein, is analoguos to a chromogenic reaction product. The fluorogenic reaction product, a fluorophore, is able to produce a fluorescent detectable signal when exposed to the proper stimulus.

"Label", as used herein, is any substance which is attached to a specific binding member or reaction product and which is capable of producing a signal that is detectable by visual or instrumental means. Various suitable labels for use in the present invention can include chromogens; catalysts; fluorescent compounds; chemiluminescent compounds; direct visual labels including colloidal metallic and non-metallic particles, dye particles, enzymes or substrates, or organic polymer latex particles; liposomes or other vesicles containing signal producing substances; and the like.

A large number of enzymes suitable for use as labels are disclosed in U.S. Pat. No. 4,275,149, columns 19–23, herein incorporated by reference. A particularly preferred enzyme/substrate signal producing system useful in the present invention is the enzyme alkaline phosphatase wherein the substrate used is nitro blue tetrazolium-5-bromo-4-chloro-3-indolyl phosphate or a derivative or analog thereof.

In an alternative signal producing system, the label can be a fluorescent compound where no enzymatic manipulation of the label is required to produce a detectable signal. Fluorescent molecules such as fluorescein, phycobiliprotein, rhodamine and their derivatives and analogs are suitable for use as labels in this reaction.

In one embodiment, a visually detectable, colored particle can be used as the label component of the indicator reagent, thereby providing for a direct colored readout of the presence or concentration of the analyte in the sample without the need for further signal producing reagents. Materials for use as the colored particles are colloidal metals, such as gold, and dye particles as disclosed in U.S. Pat. Nos. 4,313,734 and 4,373,932. The preparation and use of non-metallic colloids, such as colloidal selenium particles, are disclosed in co-owned U.S. Pat. No. 4,954,452. The use of colloidal particle labels in immunochromatography is disclosed in co-owned U.S. Pat. No. 5,120,643. Organic polymer latex particles for use as labels are disclosed in co-owned and allowed U.S. patent application Ser. No. 248,858, filed Sep. 23, 1988 (Issue Fee paid).

A "signal producing component", as used herein, refers to any substance capable of reacting with another assay reagent or the analyte to produce a labeled reaction product, which may be chromogenic, or signal that indicates the presence of the analyte and that is detectable by visual or instrumental means. "Signal production system", as used herein, refers to the group of assay reagents that are needed to produce the desired labeled reaction product or signal. For example, one or more signal producing components can be used to react with a label and generate the detectable signal, i.e., when the label is an enzyme, amplification of the detectable signal is obtained by reacting the enzyme with one or more substrates or additional enzymes to produce a detectable reaction product.

An "ancillary specific binding member", as used herein, refers to any member of a specific binding pair which is used in the assay in addition to the specific binding members of the capture reagent and the indicator reagent and which becomes a part of the final binding complex or reaction product. One or more ancillary specific binding members can be used in an assay. For example, an ancillary specific binding member can be capable of binding the analyte, as well as a second specific binding member to which the analyte itself could not attach.

Binding assays involve the specific binding of the analyte and/or an indicator reagent (comprising a label, which maybe attached to a specific binding member) to a capture reagent (comprising a second specific binding member) which immobilizes the analyte and/or indicator reagent on a support medium or which at least slows the migration of the analyte or indicator reagent through a chromatographic support medium.

The label, as described above, enables the indicator reagent or the reaction product to produce a detectable signal that is related to the amount of analyte in the test sample. The specific binding member component of the indicator reagent enables the indirect binding of the label to the analyte, to an ancillary specific binding member or to a capture reagent. The selection of a particular label is not critical, but the label will be capable of generating a detectable signal either by itself, such as a visually detectable signal generated by colored organic polymer latex particles, or in conjunction with one or more additional signal producing components, such as a chromogenic reaction product or an enzyme/substrate signal producing system. A variety of different indicator reagents can be formed by varying either the label or the specific binding member; it will be appreciated by one skilled in the art that the choice involves consideration of the analyte to be detected and the desired means of detection.

The capture reagent, in a binding assay, is used to facilitate the observation of the detectable signal by substantially separating the analyte or labeled reaction product and/or the indicator reagent from other assay reagents and the remaining components of the test sample. The capture reagent of the present invention can be a specific binding member, such as those described above. In a binding assay, the capture reagent is immobilized on the support medium to form a "capture situs", i.e., that region of the support medium having one or more capture reagents non-diffusively attached thereto.

In a binding assay a patient test bar and procedural control bar can be formed by directly or indirectly attaching their respective capture reagent to the chromatographic materials. Direct attachment methods include adsorption, absorption and covalent binding such as by use of (i) a cyanogen halide, e.g., cyanogen lormide or (ii) by use of glutaraldehyde. Depending on the assay, it may be preferred, however, to retain or immobilize the desired reagent on the chromatographic material indirectly through the use of insoluble microparticles to which the reagent has been attached. The means of attaching a reagent to the microparticles encompasses both covalent and non-covalent means, that is adhered, absorbed or adsorbed. It is preferred that capture reagents be attached to the microparticles by covalent means. By "retained and immobilized" is meant that the particles, once on the support medium, are not capable of substantial movement to positions elsewhere within the material. The particles can be selected by one skilled in the art from any suitable type of particulate material composed of polypropylene, latex, polytetrafluoroethylene, polyacrylonitrile, polycarbonate, glass or similar materials. The size of the particles is not critical, although generally it is preferred that the average diameter of the particles be smaller than the average diameter of the particles be smaller than the average port or capillary size of the chromatographic material.

The capture reagent(s), signal producing component(s) or reagent-coated microparticles can be deposited singly or in various combinations on or in the support medium in variety of configurations to produce different detection of measurement formats. For example, a reagent can be deposited as a discrete situs having an area substantially smaller than that of the entire support medium.

It is also within the scope of this invention to have a reagent; at the downstream or distal end 23 of the chromatographic material, which indicates the completion of a binding assay (i.e., end of assay indicator) by changing color upon contact with the test solution, wicking solution or a signal producing component. Reagents which would change color upon contact with a test solution containing water are the dehydrated transition metal salts, such as $CuSO_4$, $Co(NO_3)_2$, and the like. The pH indicator dyes can also be selected to respond to the pH of the buffered wicking solution. For example, phenolphthalein changes from clear to intense pink upon contact with a wicking solution having a pH range between 8.0 and 10.0, which is common pH range for the assay fluids.

Reagents can be added directly to either the application pad 21 or the chromatographic material 12 during the performance of the assay. The preferred embodiment of the invention, however, involves the incorporation of all necessary assay reagents into the assay device so that only a liquid test sample need be contacted to the application pad to perform the assay. Therefore, one or more assay reagents can be present in either or both the application pad or chromatographic material of the present invention.

In a sandwich binding assay, the migrating test solution or test sample contains both the dissolved indicator reagent from the application pad and the analyte from the test sample. Accordingly, both the indicator reagent and analyte are carried downstream by advancing liquid front. Moreover, during their migration, the indicator reagent can bind to the analyte to form an indicator reagent/analyte complex (labeled reaction product.) As the wicking liquid transports the indicator reagent/analyte complex through the chromatographic materials, the immobilized capture reagent also binds to the analyte to render the indicator reagent/analyte complex immobilized. Thus, the indicator reagent/analyte complex is able to advance only as long as capture reagent binding sites on the chromatographic material are already occupied and no longer available for further binding. Consequently, the greater the concentration of analyte in the test sample, the further the distal migration of the indicator reagent/analyte complex through the chromatographic material even- beyond the testing region.

Figure 4:
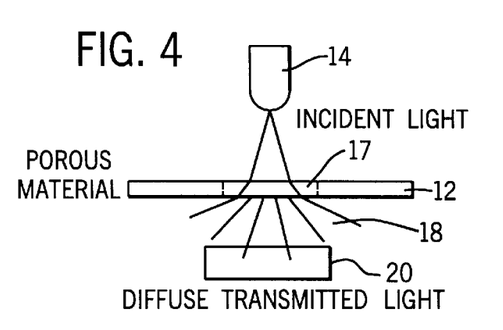
FIG. 4 illustrates the positioning of the reagent pad of FIG. 3 in a photometric determination circuit as taught in FIG. 1.

Once the sample is placed on the support medium using the above techniques, a read window 17 is defined. As shown in FIG. 4, this window is placed in position relative to the LED 14 for exposing the sample 16 to the source light in order to make a quantitative determination of the analyte.

Figure 6:
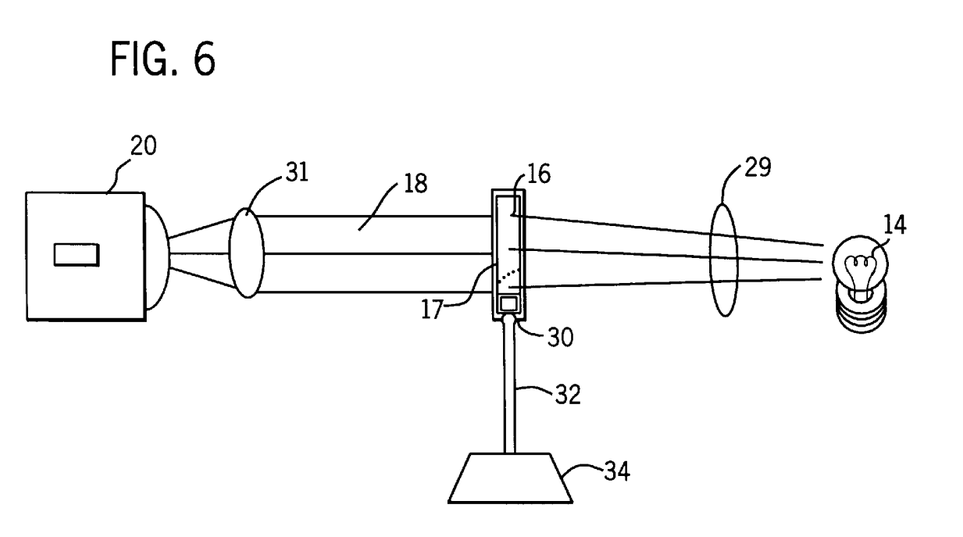
FIG. 6 shows an overall view of a reader device for the invention.

An overall view of a reader device for the invention is shown in FIG. 6. In this embodiment, a support medium 12 in strip form is place in a holder 30. The base 32 of the holder is then positioned in a receptacle 34, for accurately positioning the read window to receive the source light signal from the LED 14, as may be modified or focussed by lens 29, if desired. The scattered response light signal 18 is transmitted through the membrane and analyte is collected at the photosensitive device 20, through a lens 31, where desired. The scattered light from the membrane radiates as a uniform light source which is collected for providing the raw quantitative signal to the detector circuit.

Example 1

Hemoglobin test strip.

Reagent pads are made from glass fiber material from Lydall (code 93-1622, Lydall Inc., Hamptonville, N.C.) soaked with 2.0% sodium deoxycholate (Sigma Chemical Company, St. Louis, Mo.), 1.5% sodium nitrite (Sigma Chemical Company, St. Louis, Mo.) and 0.2% sodium azide (Sigma Chemical Company, St. Louis, Mo.), dried under forced air at 68° C. and cut into 6×4 mm rectangles. This is then laminated to 6×4 mm rectangles of nitrocellulose (5 micron, "extra surfactant", code MEM 055, Schleicher & Schuell, Keene, N.H.) with 1 mm overlap, by means of adhesive tape (AR7279, Adhesives Research Inc., Glenrock, Pa.) placed on both surfaces. The assay is run by adding 25 μl of whole blood to the end of the Lydall pad and allowing it to diffuse longitudinally into the strip. The pad saturates within 3–5 sec and the nitrocellulose takes an additional 20–35 sec. The nitrocelluose is selected from a variety of possible highly light-scattering materials because it was found to be more optically uniform. The color intensity of the fully oxidized hemoglobin is read with a prototype reader shown in FIG. 1 and using a green LED (Ledtronics Inc., Torrance, Calif., part # L200CWG5H) as light source and a photodiode (Motorola MRD711) as detector, mounted 2 mm from the strip on either side. Electronic detection was digitized as previously described in the specification. The reader was calibrated with known hemogobin standards (American Scientific Products, A Baxter Travenol Co., McGaw Park, Ill.) and unknowns were determined using a standard Coulter Counter (Coulter Electronics, Hialeah, Fla.). FIG. 6 shows the results of a correlation study with 166 samples and a correlation coefficient between the two methods was determined to be 99%.

Example 2

βHCG test strip.

Materials and reagents for these strips are obtained from the line for production of the Abbott TestPack Plus hCG. The strips are available under the tradename Advance, Advance Care Products, Ortho Diagnostics (Raritan, N.J.). Application pads, contain antiHCG conjugated with colloidal selenium, were 5 micron nitrocellulose material (Schleicher & Schuell, Keene, N.H.) containing parallell lines of anti-hCG (forming the second half of a sandwich assay) and of anti-hCG bound hCG (control bar) applied by reagent jetting. These are laminated into ribbons using the adhesive tape of example 1 and cut into strips. The resulting strips have dimensions 3 mm wide by 4 mm long; with the pad the device was 0.5 inches long and overlapped the strip approximately 1 mm. The antibody and control bars were disposed at 1 cm and 1.5 cm from the pad end of the nitrocellulose. Strips are developed by dipping the conjugate (application) pad 1 mm deep into ca. 50 μl of known βHCG standards (25, 50, 150, 250, and 500 mIU/ml). The standards, 25–250 mIU/ml, were obtained by mixing combinations of the 0, 50, and 250 mIU/ml hCG-Urine controls (Abbott Laboratories, Abbott Park, Ill., Product No. 3A28-02). The 500 mIU/ml standard was obtained from Abbott TestPack hCG-Urine controls (Abbott Laboratories, Abbott Park, Ill., No. 1196-02) as provided with the Abbott TestPack hCG kit. Ten strips were run for each concentration except for 25 mIU (n=9). The strips were read using a scanning transmission densitometer using a LED (570 nm) light source, a phototransistor detector with a circular aperture (0.5 mm diameter). The transmission densitometer was a prototype constructed as described in Example 1, except that a 12 bit analog to digital converter was used to measure the output from the phototransistor.

Figure 5:
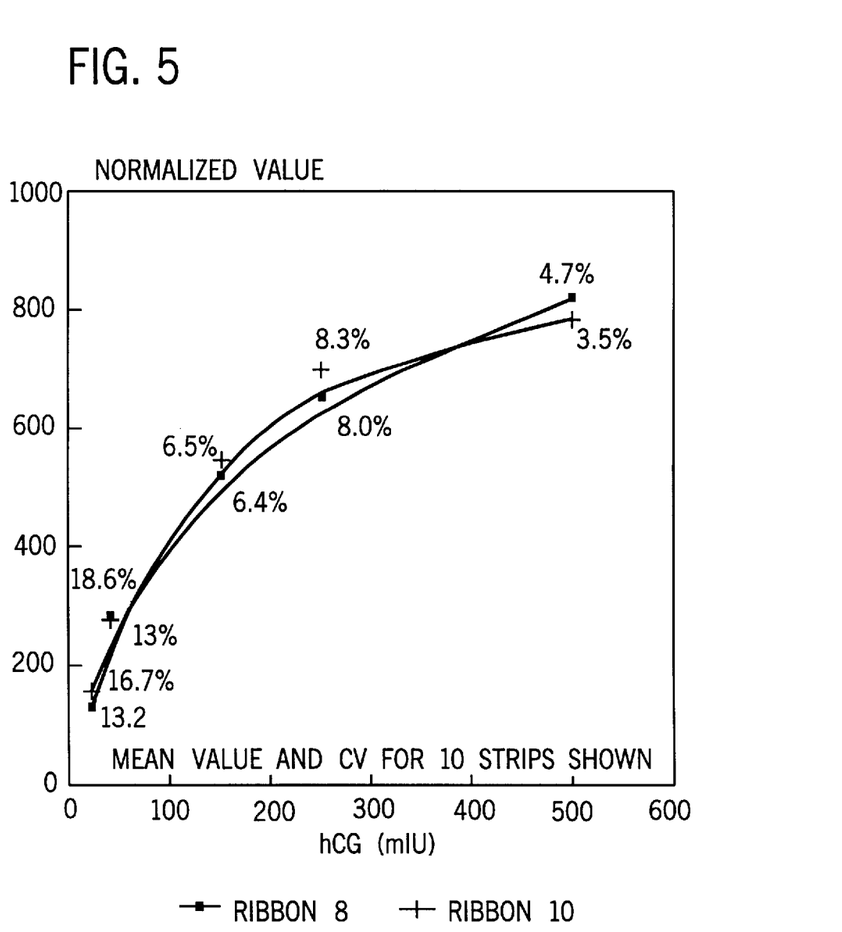
FIG. 5 shows a summary set of data for an hCG titration curve obtained with an immunochromatographic strip based sandwich assay obtained using the teachings of the subject invention.

The mean values of the normalized signals are plotted in FIG. 5 along with the corresponding CVs. The relative intensities of the two bands are determined with a similar reader to that of Example 1, except with the provision of a spring-loaded dashpot device to provide transport of the detector across the region of the two developed bands.

Intensity data points are collected every ca. 0.25 msec. for a total scan time of ca.1 second and averaged into groups of 16. The data was finally analysed by correcting peak heights for means of minimum readings in regions adjacent to each of the two bands, and expressed as a ratio of the two thus corrected peak heights. A typical plot of concentration against β ratio is shown in FIG. 5.

Example 3

Test strips for quantitation of DNA amplification products.

DNA for exons 45 and 51 of the dystrophin gene are amplified by standard PCR multiplex amplification [Chamberlain J S,. Gibbs R A, Rainer J E Nguyen P N & Caskey CTW, Nucleic Acids Research, 16, 1141–1156 (1988)], with the exception that the primers utilized were are labelled terminally with the following haptens: forward primers are biotinylated via sulfosuccinimidyl biotinamido hexanoate on to 5' amino-modified termini. Of the reverse primers, that for exon 51 is fluorescenated and that for exon 45 is deriviatized with theophylline by similar standard methods. The corresponding PCR products then are dually haptenated and can be quantitated by immunological sandwich assays in test strips as follows. Mouse monoclonal anti-fluorescein, 1 mg/ml (Abbott Laboratories, Abbott Park, Ill., No. 2-572-126) and anti-theophylline, 0.75 mg/ml (Biospecific, Emeryville, Calif.) in 100 mM Tris buffered saline (Abbott Laboratories, Abbott Park, Ill., No. 99521) and 0.1% bovine serum albumin (Irvine Scientific, Santa Ana, Calif.), 1% sucrose (BioRad, Richmond, Calif.), are dispensed in lines of 0.25 mm width on $5\mu$ nitrocellulose as in the preceeding examples) by reagent jetting at 0.6 $\mu l/mm^2$ of antibody solution. Colloidal selenium as in preceeding examples was coated with rabbit anti-biotin, 7 optical density units, at a wavelength of 550 nm, of selenium and 1 $\mu g/ml$ of antibody. PCR products are diluted 6-fold into the conjugate with 3% alkaline treated casein (U.S. Pat. No. 5,120,643) and 30 $\mu l$ chromatographed up the strips for 5 min. Dual band scans are performed as in the preceeding example. Results were obtained for normal individuals and individuals with carrier staus for exon 51 but not 45. Results obtained are as follows:

| Sample identification | Signal ratio |
|---|---|
| Normals | |
| 5354 | 1.14 |
| 9171 | 0.90 |
| 9694 | 1.06 |
| Carriers | |
| 5395 | 0.64 |
| 6784 | 0.65 |
| 7274 | 0.52 |
| 9693 | 0.63 |

An example determination using the teachings of the subject invention is shown in FIG. 5, for an hCG titration curve obtained with an immunochromatographic strip based sandwich assay.

Example 4

(Paper example, this example is based on the publication Lou, S. C. et. al., Clin. Chem., 39/4, 691–624, 1993.)

A quantitative whole blood test for Lp(a), a predictor for artery disease could be produced as follows: A selenium conjugate is prepared by mixing 1 ml selenium colloid (maximum optical density 15 at 540 nm) with 10 ug of Lp(a) protein (A. M. Scanu, University of Chicago, Chicago, Ill.).

The reagent pad is a 0.8×0.3 cm piece of glass fiber matrix (Lydall, Inc., Hamptonville, N.C.) soaked in Lp(a) conjugate, anti-erythrocyte antiseruml mg/ml, (such as from United States Biochemical Corp., Cleveland, Ohio), and casein, 20 mg/ml ( such as from Abbott Laboratories, Abbott Park, Ill., No. 95024) and then dried using forced air (10 cm/sec) at room temperature. The reagent pad is attached to a nitrocellulose membrane (5×0.3 cm) to which anti-Lp(a) monoclonal antibody (Abbott Laboratories, Abbott Park, Ill., No. 8B4) is applied. The area of immobilized anti-Lp(a) antibody on the nitrocellulose membrane defines the conjugate capture site and transmission read area. Immunochromatography would then be carried out by applying a whole blood sample to the reagent pad. The red blood cells are trapped in the reagent pad by the action of the anti-erythrocyte antiserm and the filtration properties of the glass fiber matrix. The resulting mixture of plasma and conjugate migrates up the strip. If no Lp(a) is present in the sample then the conjugate accumulates at the capture/read site and transmission of light through this site will be reduced accordingly. When Lp(a) is present in the sample it prevents binding of the conjugate and results in a reduced accumulation at the capture site and, hence, more light is transmitted than when Lp(a) is not present. The amount of light passing through the capture site could be measured using a scanning reader as described in example 2. The increase in transmission of light could be correlated to the increase in Lp(a) in the patient sample to provide a quantative result.

Example 5

Another example of a clinical chemistry type assay that could be performed in this format is a whole blood cholesterol test. For example, a reagent pad containing anti-erythocyte antiserum, 1 mg/ml (United States Biochemical Corp., Cleveland, Ohio), and a 10X concentrated solution of cholesterol reagent, such as AGENT Cholesterol (Abbott Laboratories, Abbott Park, Ill., No. 6095-02) to a membrane as in Example 1. Such a test could accept a blood sample produced by a finger stick. The Red Blood Cells (RBC) would be removed from the sample by the action of the anti-RBC in combination with the filtration effects of the reagent pad (as in example 4). The resulting plasma mixed with AGENT cholesterol reagents would wick into the membrane read area. The resulting color development in the membrane, absorption maximum at 500 nm for the AGENT reagents, is proportional to the cholesterol concentration and would be measured as described in Example 1. Another example of a clinical chemistry type that could be performed in this format is a glucose assay.

While certain features and embodiments of the invention have been shown and described in detail herein, it will be readily understood that the invention encompasses all modifications and enhancements within the scope of the following claims.

What is claimed is:

1. An apparatus for making a quantitative determination of the amount of an analyte in a biological sample comprising:

a. a support medium for receiving a biological sample and retaining a labeled reaction product thereon, the medium including a read window capable of receiving a source light signal and transmitting therethrough a response light signal that has been altered from the source light signal by the presence of a labeled reaction product, wherein said medium is highly light-scattering, the amount of said alteration of said response light signal by said labeled reaction product being an indication of the amount of said analyte in said biological sample;

b. a source of light positioned to transmit a source light signal to the read window of the medium and to the labeled reaction product at the read window, whereby the response light signal is produced;

c. a collector positioned to receive the response light signal transmitted from the read window of the medium, said collector capable of developing a variable output signal in direct correspondence to the intensity of the response light signal, said collector being a photosensitive element; and d. means for measuring the variable output signal and correlating the measured signal to the amount of analyte in the sample, said means for measuring the variable output signal comprising:

(1) a capacitor network connected in series with the photosensitive element, said capacitor network comprising a capacitor, said capacitor network having a discharge cycle over a time cycled duration;

(2) a power source coupled to the capacitor network and the photosensitive element and capable of charging the capacitor network: and (3) means for measuring the duration of the discharge cycle of the capacitor network through the resistance developed by the photosensitive element in response to the intensity of the response light signal, wherein the light intensity of the response light signal is related to the duration of the discharge cycle.

2. The apparatus of claim 1, further including a switching element for selectively activating and deactivating the capacitor network.

3. The apparatus of claim 2, wherein the switching element is a transistor switch capable of allowing the capacitor network to discharge when the transistor is in the ON condition.

4. The apparatus of claim 1, wherein the photosensitive element is a phototransistor.

5. The apparatus of claim 1, wherein the switching element is in parallel with the capacitor network.

6. The apparatus of claim 1, wherein the means for measuring the duration of the discharge cycle comprises a comparator having a reference level signal against which the response light signal is compared to a reference point to determine the intensity of the response light signal.

7. The apparatus of claim 1, wherein the light intensity of the response light signal is directly proportional to the duration of the charge cycle of the capacitor network.

8. The apparatus of claim 1, wherein the source of light is positioned on one side of the support medium and the collector is positioned on the other side of the support medium for receiving the response light signal transmitted therethrough, said source of light and said collector positioned in line with said read window.

9. The apparatus of claim 1, wherein the support medium is a nitrocellulose membrane.

10. The apparatus of claim 1, wherein the label of the labeled reaction product is a chromogen.

11. The apparatus of claim 10, wherein the chromogenic reaction product is the product formed as the result of a chemical or immunological reaction between the analyte or an analog of the analyte and a reagent used in the assay.

12. The apparatus of claim 11, wherein the chromogenic reaction product is an immunologically bound reaction product.

13. The apparatus of claim 1, wherein the analyte is hemoglobin.

14. The apparatus of claim 1, wherein the analyte is cholesterol.

15. The apparatus of claim 1, wherein the analyte is glucose.

16. A method of determination the amount of an analyte present in a liquid biological sample comprising:

a. providing a highly light-scattering support medium for receiving a liquid, analyte-containing biological sample and for retaining thereon a labeled reaction product, said support medium having a read window, said read window being positioned between a source light emitter and a collector, said collector being a photosensitive element;

b. combining said sample with one or more reagents to produce a labeled reaction product, wherein at least one of said one or more reagents is a substance capable of reacting with another assay reagent or the analyte to produce a labeled reaction product or signal that indicates the presence of the analyte and that is detectable by visual or instrumental means;

c. retaining said labeled reaction product on said support medium;

d. exposing said labeled reaction product and said support medium to said source of light whereby there is transmitted through said support medium a response light signal altered from the source of light by the presence of the labeled reaction product, the amount of said alteration of said response light signal by said labeled reaction product being an indication of the amount of analyte in said biological sample;

e. measuring the intensity of the response light signal by generating a variable resistance signal that corresponds to the intensity of the response light signal, said variable resistance signal being measured by a measuring means comprising:

(1) a capacitor network connected in series with the photosensitive element, said capacitor network comprising a capacitor, said capacitor network having a discharge cycle over a time cycled duration:

(2) a power source coupled to the capacitor network and the photosensitive element and capable of charging the capacitor network; and (3) means for measuring the duration of the discharge cycle of the capacitor network through the resistance developed by the photosensitive element in response to the intensity of the response light signal, wherein the light intensity of the response light signal is related to the duration of the discharge cycle; and f. correlating the intensity of said response light signal to the amount of analyte in the sample.

17. The method of claim 16, wherein the support medium is formed from a chromatographic medium.

18. The method of claim 16, wherein the generation of said variable resistance signal comprises:

a. charging a capacitor network connected in series with the photosensitive element; and b. measuring the duration of the discharge cycle of the capacitor network through the resistance developed by the photosensitive element in response to the intensity of the response light signal.

19. The method of claim 18, wherein the photosensitive element is a phototransistor.

20. The method of claim 18, wherein the measuring step includes comparing the time duration of the discharge cycle with a reference time corresponding to a predetermined amount of chromogenic reaction product.

21. The method of claim 18, wherein the light intensity of the response light signal is directly proportional to the duration of the charge cycle of the capacitor network.

22. The method of claim 16, wherein the support medium is a nitrocellulose membrane.

23. The method of claim 16, wherein the labeled reaction product is the product formed as the result of a chemical or immunological reaction between the analyte or an analog of the analyte and a reagent used in the assay.

24. The method of claim 16, wherein the analye is hemoglobin.

25. The method of claim 16, wherein the analye is cholesterol.

26. The method of claim 16, wherein the analyte is glucose.

27. The method of claim 16, wherein at least one of said reagents for the labeled reaction product is a member of a specific binding pair.

28. The method of claim 16, wherein the labeled reaction product is an immunologically bound reaction product.

29. The method of claim 16, wherein the combining of the sample and one or more of said reagents is performed within said support medium.

30. The method of claim 16, wherein said sample and at least one of said one or more reagents are combined external to said support medium.

31. The method of claim 16, wherein said support medium contains a predetermined amount of at least one of said one or more reagents.

32. The method of claim 16, wherein the label of said labeled reaction product is a chromogen.

33. The method of claim 16, wherein the label of said labeled reaction product is fluorogenic.

34. The method of claim 33, wherein the fluorogenic label is an enzyme.

35. The method of claim 16, wherein the label of said labeled reaction product is a particle.

36. The method of claim 35, wherein the particle is colored.

37. The method of claim 35, wherein the particle is a colloidal metal.

38. The method of claim 35, wherein the particle is non-metallic.

* * * * *

UNITED STATES PATENT AND TRADEMARK OFFICE
CERTIFICATE OF CORRECTION

PATENT NO. : 5,770,389
DATED : June 23, 1998
INVENTOR(S) : Ching et al.

It is certified that error appears in the above-identified patent and that said Letters Patent is hereby corrected as shown below:

Column 13, line 23, change ":" to --;--.

Column 14, line 40, change ":" to --;--.

Signed and Sealed this

Third Day of November, 1998

Attest:

Attesting Officer

BRUCE LEHMAN
Commissioner of Patents and Trademarks